United States Patent [19]

Rosen

[11] Patent Number: 4,946,455
[45] Date of Patent: Aug. 7, 1990

[54] MEDICAL TUBING CONNECTOR

[76] Inventor: Robert J. Rosen, 291 Church Street, New York, N.Y. 10013

[21] Appl. No.: 276,151

[22] Filed: Nov. 25, 1988

[51] Int. Cl.$^5$ .............................................. A61M 5/14
[52] U.S. Cl. .................................. 604/403; 604/905; 137/614.04
[58] Field of Search .............................. 604/403, 905; 137/614.04

[56] References Cited

U.S. PATENT DOCUMENTS

| | | |
|---|---|---|
| 109,695 | 11/1870 | Westinghouse, Jr. |
| 3,176,717 | 4/1965 | Ogne ............................... 137/614.02 |
| 3,217,746 | 11/1965 | Voisine ........................... 137/614.04 |
| 3,289,700 | 12/1966 | Gildone ........................... 137/614.04 |
| 3,394,954 | 7/1968 | Sarns ............................... 604/905 X |
| 4,106,523 | 8/1978 | Thornton, et al. .............. 137/614.04 |
| 4,256,106 | 3/1981 | Shoor . |
| 4,327,770 | 5/1982 | Brown et al. ................... 137/614.05 |
| 4,334,551 | 6/1982 | Pfister ............................. 137/614.03 |
| 4,433,973 | 2/1984 | Kurtz et al. ......................... 604/403 |
| 4,465,096 | 8/1984 | Voisine ........................... 137/614.04 |
| 4,485,845 | 12/1984 | Brady ............................. 137/614.04 |
| 4,610,469 | 9/1986 | Wolff-Mooij ....................... 285/260 |
| 4,683,916 | 8/1987 | Raines ............................. 137/854 |

Primary Examiner—C. Fred Rosenbaum
Assistant Examiner—C. Maglione
Attorney, Agent, or Firm—Woodard, Emhardt, Naughton, Moriarty & McNett

[57] ABSTRACT

A medical tubing connector includes an elongated generally cylindrical housing for universal coupling to an identically configured connector. The housing includes an open connecting end, a nozzle for connecting to sterile medical tubing and a base portion defining a fluid passageway from the nozzle. A valve assembly is disposed within the connector. The housing also includes an interconnecting portion between the open end and the base portion that comprises a pair of diametrically opposite fingers. The fingers are spaced circumferentially apart to define complementary slots interspersed therebetween. The fingers and slots are configured for engagement when a pair of connectors are interengaged to form a sterile enclosure about the valve assemblies of each connector. The valve assembly for each connector includes a piston that slides within the interlocking portion and contacts several piston retaining stops near the open end of the housing to keep the valve assembly within the housing. The piston also includes a plunger having a feed orifice in its outer surface that communicates with a bore extending along the length of the plunger. The bore opens at a coupling port in a coupling face at the other end of the piston. The coupling face contacts the coupling face of another connector when a pair of connectors are interengaged. A coupling O-ring surrounds the coupling port and is adapted to form a sealed fluid connection when the coupling faces contact. A collar and O-ring are mounted in the fluid passageway with the plunger passing therethrough. The piston is spring biased to a normally closed position, in which the feed orifice is sealed from the fluid passageway by the collar and the sealring. When the pair of connectors are interengaged with the complementary fingers and slots connected, the piston is in an open position in which the feed orifice is in fluid connection with the fluid passageway and the coupling faces remaining in sealed fluid connection.

9 Claims, 2 Drawing Sheets

MEDICAL TUBING CONNECTOR

BACKGROUND OF THE INVENTION

The present invention relates to the field of fluid connectors for the sterile connection of medical tubing.

In medical care and research, reusable connection of medical tubing is often required. In many medical applications, such as those involving catheterization of a patient, it is essential that each element in the fluid flow path maintain sterile integrity. For instance, in I.V. applications, a sterile fluid source is frequently connected and disconnected from a body resident catheter.

It is, therefore, very important that a fluid connector assembly be provided that is easily interengaged and that provides a positive sterile, leak-free fluid coupling. Leakage from the connector poses a risk to the patient and to medical personnel, particularly in cases involving highly contagious or communicable diseases. Likewise, contamination of the fluid coupling of the connector during use and from contact with non-sterile objects when disconnected, presents a risk to the patient.

SUMMARY OF THE INVENTION

In view of the risks incumbent with medical tubing connectors, and in view of the limitations of previous connectors in meeting these risks, the present invention provides a universal connector that meets the needs of this field. In one embodiment of the invention, a universal fluid connector assembly includes a pair of identically constructed interengageable connectors. Each of the connectors includes a housing having an open connecting end, a nozzle for connection to sterile tubing and a base portion defining a fluid passageway therethrough from the nozzle. A valve assembly is disposed within the housing and is movable from a position in which fluid is communicated through the fluid passageway and the valve assembly, and a position in which fluid flow is restricted.

In an important feature of the invention, the housing includes an interlocking portion between the open end of the housing and the base portion and having a number of fingers equally perimetrically spaced around the housing with an equal number of complementary slots therebetween. The fingers of one connector of the pair fits into the slots of another connector, and vice versa, to establish an enclosure around the valve assemblies of both connectors.

The valve assembly for each connector includes a piston that is movable relative to the housing and has a feed orifice at one end of the piston and a coupling face with a coupling port at the other end of the piston. A conduit within the piston communicates between the feed orifice and the coupling port. A sealring and collar mounted in the fluid passageway seal the feed orifice from the fluid passageway when the piston is in a closed position. A spring reacting between the collar and the piston biases the piston to the closed position. The feed orifice in the piston communicates with the fluid passageway when the piston is depressed against the spring so that the feed orifice moves past the sealring and collar.

In another feature of the invention, as the pair of connectors are moved towards one another, the coupling faces of the pistons contact to establish a sealing engagement between the coupling faces and to establish a fluid connection between the respective coupling ports of the coupling faces. As the pair of connectors are moved further towards one another the coupling face of the pistons remain in contact with one another as the pistons move relative to their respective housings, from the closed position to an open position in which the fluid passageway and the feed orifice are in fluid communication for each of the pair of connectors.

It is one object of the present invention to provide a sterile medical connector that is universal, that is a connector assembly in which each of the connector halves are of identical construction. A further object of the invention is to provide a connector that is self-sealing on disconnect, and that provides a positive sterile, a leak-free fluid coupling when a pair of connectors are connected.

One object of the invention is to provide a connector with that protects the fluid coupling from physical contact with non-sterile objects when the connector is disengaged from another connector. It is another object of the invention to provide a medical connector that provides the ability to purge or bleed the fluid line without engaging the connector.

Other objects and benefits of this invention will come to light in reveiwing the following written specification and accompanying drawings.

DESCRIPTION OF THE PREFERRED EMBODIMENT

Figure 1:
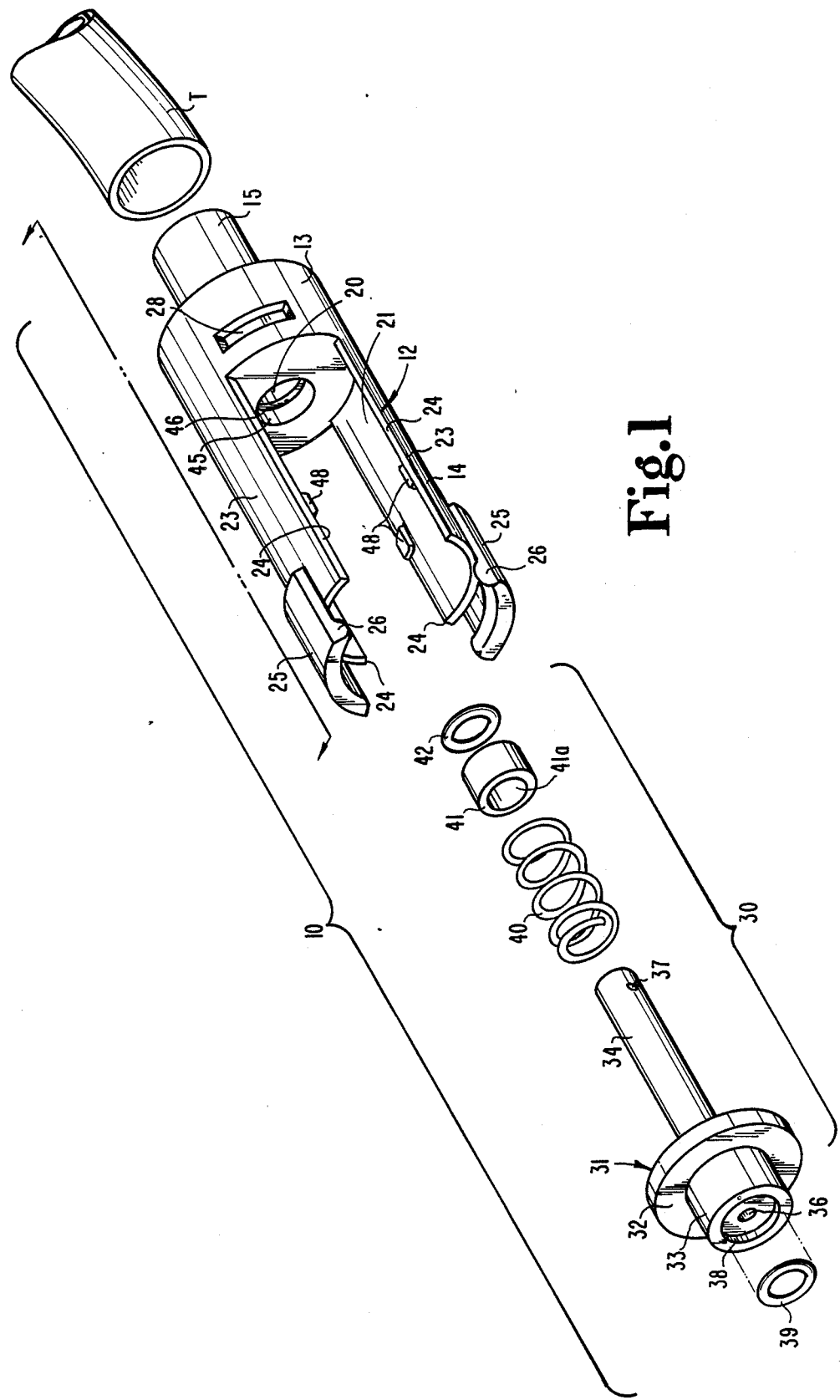
FIG. 1 is an exploded perspective view of the medical tubing connectors for sterile tubing of the present invention.

For the purposes of promoting an understanding of the principles of the invention, reference will now be made to the embodiment illustrated in the drawings and specific language will be used to described the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
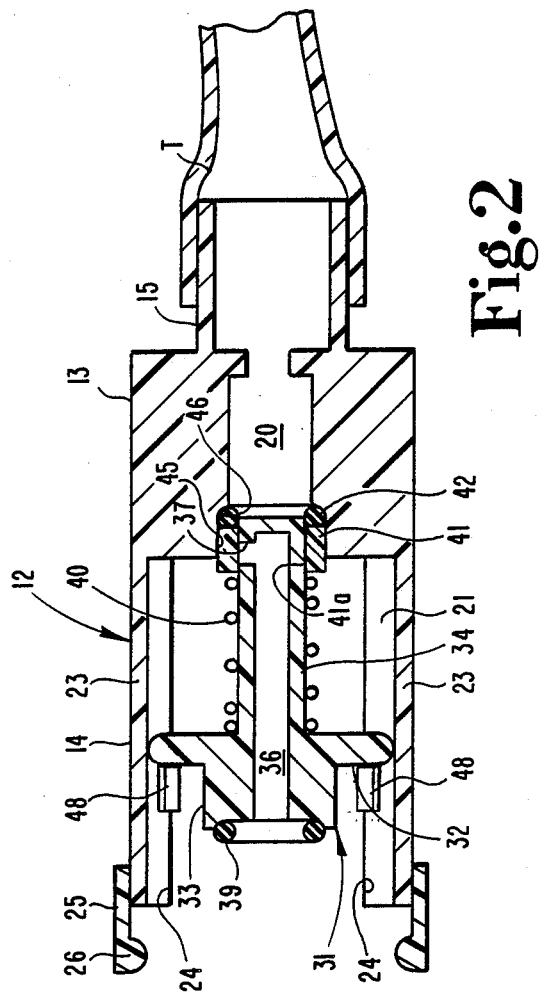
FIG. 2 is a cross sectional view of the medical tubing connector of FIG. 1 taken along line 2—2 as viewed in the direction of the arrows, shown in the fully assembled configuration.

A universal fluid connector assembly 10 includes an elongated cylindrical housing 12, as illustrated in the exploded diagram of FIG. 1. The housing 12 includes a base portion 13, with an interconnecting portion 14 and a tube attachment nozzle 15 projecting from opposite faces of the base portion. A fluid passageway 20 is defined within the base portion 13 and tube attachment nozzle 15, as shown in FIG. 2. the tube attachment nozzle 15 is adapted to engage a sterile medical tube T to allow fluid to flow to and from the universal fluid connector 10 and the tube T. The interconnecting portion 14 has an open end opposite its interface with the base portion 13, and defines a discontinuous interior surface 21. When the interconnecting portion of one connector is engaged over the open end of the portion 14 of another connector, the surfaces 21 of each connector combine to form a continuous interior surface and an enclosed interior for the fluid coupling between the two connectors.

The interconnecting portion 14 includes, in the preferred embodiment, a pair of interlocking fingers 23. Each of the interlocking finger 23 has a pair of parallel longitudinal edges 24. The edges 24 of the circumferentially spaced apart fingers 23 define complementary slots between the fingers. The circumferential distance between the edges 24 of adjacent fingers 23 is equal to the cirumferential width of each of the interlocking fingers. Consequently, the interlocking fingers of a second connector can fit into the slots of a first connector, and vice versa. While the preferred embodiment of the universal fluid connector of the present invention includes two interlocking fingers and two slots interspersed therebetween, a greater number of slots and fingers may be provided. It is, however, important that the housing 12 include at least two interlocking fingers 23 to provide protection for the valve assembly 30 (described in more detail herein) situated within the housing when the connector is decoupled or disengaged. The fingers 23 surround the valve assembly 30 to prevent contact between the fluid coupling features of the valve assembly and non-sterile object if, for instance, the connector is dropped.

Each of the interlocking fingers 23 includes a connecting clip 25 attached at the free end of the finger. The connecting clip 25 includes an inwardly projecting tab 26. The base portion 13 includes a locking recess 28 that is sized to fit a tab 26. The locking recess is circumferentially situated between the interlocking fingers 23 of the housing 12, or longitudinally in line with the slots formed between the fingers. Thus, when a pair of universal fluid connectors are interengaged, the connecting clips 25 and tab 26 of each of the connectors snap into the corresponding locking recesses 28 of the pair of connectors. The pair of universal fluid connectors can be disengaged by prying the tabs 26 from the locking recesses 28. In addition, the shape of the tabs 26 can be slightly rounded so that the tabs can be disengaged from the locking recesses 28 by pulling the pair of connectors apart with a pre-determined amount of longitudinal force.

The universal fluid connector assembly 10 includes a fluid coupling or valve assembly 30, shown in an exploded view in FIG. 1 and in its normally closed position within the housing 12 in FIG. 2. The valve assembly 30 includes a piston 31 having a disc 32 that is sized to slidingly contact the interior surface 21 of the interconnecting portion 14. The piston 31 includes a piston head 33 projecting from the disc 32 toward the open end of the housing 12. The exposed face 33a of the piston head 33, in the normally closed position, is situated inward from the open end of the housing to prevent contamination of the fluid coupling elements of the valve assembly. Projecting from the opposite face of the disc 32 is a plunger 34. A bore 36 extends through the piston 31 from the exposed face 33a of the piston head 33 nearly to the free end 34a of the plunger 34. The free end 34a of the plunger is closed. However, a feed orifice 37 is formed near the end of the plunger 34, projecting radially inward to create a flow path to the bore 36.

Surrounding the opening of the bore 36 in the exposed face 33a of the piston head 33 is an O-ring groove 38. A coupling O-ring 39 is mounted within the O-ring groove 38, and preferably retained by an adhesive to prevent the O-ring from becoming disengaged from the groove 38. In the valve assembly 30, the plunger 34 extends through a spring 40, a collar 41, and a second O-ring 42. As shown in FIG. 2, in the fully assembled configuration, the second O-ring 42 is seated against a sealing shoulder 46 in the base portion 13 of the housing 12. The collar 41 is disposed within a collar seat 45 in the base portion 13, and is intended to retain the second O-ring 42 in sealing egagement with the shoulder 46.

In the assembled configuration, the piston 31 is pressed into the interconnecting portion 14 of the housing, with the front face 32a of the piston disc 32 engaged against piston retaining stops 48 formed on the interior surface 21 of the interconnecting portion. The spring 40 reacts against the collar 41 and the back face 32b of the piston disc 32 to press the front face 32a of the piston disc against the stops 48 and to press the collar 41 against the second O-ring 42. The second O-ring 42 expand radially against the plunger 34 under pressure from the collar 41 and spring 40 to form a tight fluid seal against shoulder 46. The sealing pressure on the second O-ring is maintained by the spring whether the valve assembly is open or closed.

The valve assembly 30 is biased to a normally closed position by the spring 40, as illustrated in FIG. 2, in which the feed orifice 37 is situated within the collar 41. A sealing bore 41A of the collar 41 essentially seals the feed orifice 37 to prevent fluid flow through the bore 36 of the valve assembly 30. Moreover, the second O-ring 42 seals between the plunger and the shoulder 46 as indicated above. Thus, in the normally closed configuration, fluid flowing from the tube T and into the fluid passageway 20 of the housing 12 terminates at the collar 41, second O-ring 42 and the free end 34a of the piston plunger 34.

Figure 3:
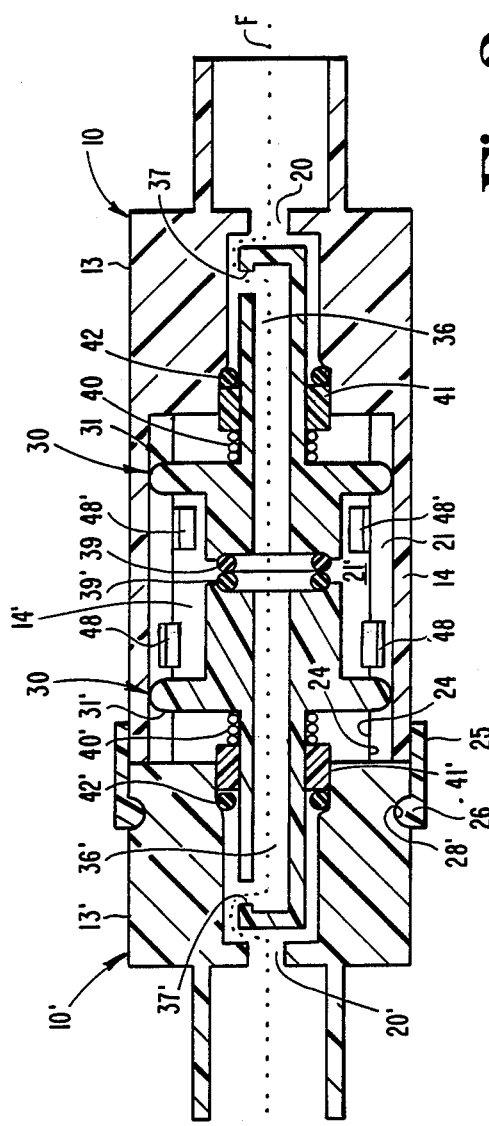
FIG. 3 is a cross sectional view of a pair of interengaged medical tubing connectors of the type illustrated in the previous figures.

With reference to FIG. 3, the operation of the sterile medical connector of the present invention is illustrated by the connection of a first universal fluid connector assembly 10 with a second connector assembly 10'. Each of the features of the second connector assembly 10' is identical to the features of the connector assembly 10 just described. For clarity, the features of the second connector 10' have been identified with a prime (') symbol adjacent the feature identification number.

When the first and second connector assemblies 10 and 10', respectively, are interengaged, the connecting clips 25 and tabs 26 of the first connector 10 shap into the locking recesses 28' of thee second connector 10'. Likewise, the connecting clips 25' and tabs 26' of the second connector lock into the recesses 28 of the first connector 10, although this engagement is not shown in FIG. 3 because this interface between the clips of the second connector and recesses of the first connector are at 90° to the clip-recess interface shown FIG. 3. When the first and second connector assemblies are interengaged, the respective finger edges 24 and 24' contact each other so that the respective interior surfaces 21 and 21' form a continuous interior surface and a completely enclosed volume about the valve assemblies 30 and 30'.

When the first and second connector assemblies are interengaged, the exposed faces of the fluid coupling O-ring 39 and 39' contact. Since the coupling O-rings are composed of a resilient material, a complete seal is formed between the two O-rings as the O-rings depress slightly and expand raadially under contact pressure. As the connectors are moved into complete interengagement, the spring 40 and and 40' of the two assemblies are gradually compressed. As the springs are compressed, they react against the collars 41 and 41' which press the second O-rings 42 and 42' against their respective sealing shoulders 46 and 46' to form a tight seal, in the manner described above.

As the two connector assemblies 10 and 10' are pressed into engagement, the piston 31 and 31' move away from the piston retainer stops 48 and 48', respectively, and longitudinally toward the fluid passageways 20 and 20'. The piston plungers 34 and 34' are stroked until the feed orifices 37 and 37' in the plungers move past the collars 41 and 41', thereby allowing fluid to flow into the valve assembly bores 36 and 36'. When the pair of fluid connector assemblies 10 and 10' are fully engaged, a fluid flow path F is opened between the connectors.

When the pair of fluid connector assemblies are disengaged, the springs 40 and 40' of the connector assemblies gradually force the pistons 31 and 31' against their respective valve stops 48 and 48'. However, the coupling O-rings 39 and 39' remain sealed against each other while the fluid connector assemblies are being disengaged, thereby preventing any leakage from the connector assembly until the feed orifices 37 and 37' are situated completely within the collars 41 and 41' and fluid flow into the respective bores 36 and 36' has been terminated. Consequently, the fluid connector assemblies of the present invention are self-sealing when disengaged. Since the piston 31 is exposed between the interlocking fingers 23 of the connector assembly, the piston 31 can be manually moved from the closed position, shown at FIG. 2, to the open position, shown at FIG. 3, in order to bleed or purge the fluid passageway 20 and associated tubing T of any excess fluid.

In the preferred embodiment, each of the working components of the medical tubing connector 10 is composed of a molded medical grade plastic. The O-rings 39 and 42 may be composed of an elastomeric material, such as rubber, or a flexible molded plastic. The spring 40 is preferably formed of a resilient plastic.

The universal fluid connector assembly of the present invention provides a sterile connection of medical tubing without leakage. The spring and O-ring design provides positive sealing between the valve assemblies of engaged connector assemblies so that fluid can flow without leakage between the valve assemblies. The universal fluid connector assembly of the present invention also provides a quick and efficient method of interengaging and disengaging a first and second connector assembly without the use of the male and female connectors of the prior art. The interlocking fingers provide protection for the valve assembly in the event that the fluid connector assembly is dropped. Moreover, the connecting clips and tabs provide a reliable positive locking feature between coupled connector assemblies that is readily engaged and disengaged with a minimum of effort.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

The invention claimed is:

1. A universal medical connector assembly for sterile connection of medical tubing, comprising:
    a pair of interengageable connectors, each of said pair of connectors being of identical construction and including;
        an elongated housing having an open connecting end, a nozzle for connection to a tube, and a base portion defining a fluid passageway therethrough from said nozzle;
        said housing further having an interlocking portion between said base portion and said open connecting end, said interlocking portion including at least two fingers equally perimetrically spaced about said housing, each of said at least two fingers having an inner surface, said several fingers defining an equal number of complementary slots perimeterically interspersed between said at least two fingers;
        a valve assembly disposed within said housing and including;
            a piston movable relative to said housing and having opposite ends with a feed orifice at one end for communicating with said fluid passageway, a coupling face at the other end with a coupling port therein and a bore between said feed orifice and said coupling port for communicating fluid therebetween;
            valve means, associated with said base portion, for controlling fluid flow between said fluid passageway in said base portion and said feed orifice in said piston; and
            biasing means for biasing said piston to a closed position in which said valve means is operable to restrict fluid flow between said fluid passageway and said feed orifice;
    whereby, when said pair of connectors are moved towards one another, said at least two fingers of each one of said pair of connectors fit within the complementary slots of the other of said pair of connectors in juxtaposed relation with and substantially contacting the fingers of the other of said pair of connectors so that the inner surfaces of each of said at least two fingers of each of said pair of connectors form a continuous inner surface defining an enclosure about said valve assemblies of each of said pair of connectors;
    whereby, as said pair of connectors are moved towards one another, the coupling faces of the pistons corresponding to one each of said pair of connectors contact to establish a sealing engagement between said coupling faces and to establish a fluid connection between the respective coupling ports of said coupling faces, and
    further whereby as said pair of connectors are moved towards one another the coupling face of the piston of each of said pair of connectors remain in contact with one another as the piston of each of said pair of connectors moves relative to the respective housing of each of said connectors, from said closed position to an open position in which said fluid passageway and said feed orifice are in fluid communication for each of said pair of connectors.

2. The universal medical connector assembly of claim 1, wherein said coupling face of said piston of each of said pair of connectors includes a resilient sealring around said coupling port.

3. The universal medical connector assembly of claim 1, wherein:
    each of said pair of connectors includes locking means for retaining said pair of connectors in interengagement, said locking means including;
        at least two resilient connecting clips corresponding to said at least two fingers, one end of each of said several clips attached to one each of said at least two fingers at said open connecting end of said housing, and a free end of each of said at least two clips having an inwardly projecting tab; and at least two locking recesses corresponding to said equal number of complementary slots, each of said at least two locking recesses aligned with a corresponding one of said slots and each of said at least two locking recesses having a shape corresponding to said inwardly projecting tab to receive said tab therein in locking engagement when said pair of connectors are interengaged.

4. The universal medical connector of claim 1, further comprising:

at least one piston retaining stop projecting inwardly from said inner surface of at least one of said at least two fingers near said open connecting end, wherein said at least one piston retaining stop is sized to prevent said piston from moving past the retaining stop toward said open end, and wherein in said closed position said biasing means holds said piston in contact with said at least one piston retaining stop.

5. The universal medical connector of claim 1, wherein:

said piston includes a piston head having said coupling face and said coupling port thereon, and a plunger projecting from said piston head and having a circumferentail surface with said feed orifice therethrough;

said valve means includes a collar and a sealring mounted in said fluid passageway with said plunger slidably extending therethrough in a tight-fitting relationship; and said biasing means includes a spring between said piston head and said collar, wherein, in said closed position, said spring is extended and said feed orifice is within said collar, and in said open position, said spring is compressed and said feed orfice is within said fluid passageway.

6. The universal medical connector assembly of claim 1, wherein:

each of said at least two fingers has a free edge distal said base portion;

said base portion includes an engagement surface at each of said complementary slots, whereby said free edge of each of said at least two fingers is disposed adjacent said engagement surface at each of said complementary slots when said connectors are interengaged; and said connector assembly includes means for preventing said coupling face of said piston from extending outside a plane defined by said free edge of said at least two fingers.

7. The universal medical connector assembly of claim 5, wherein:

said base portion includes a sealing shoulder around said fluid passageway;

said sealring contacts said sealring shoulder; and said collar contacts said sealring, whereby said spring acts against said collar to cause said collar to press said sealring between said collar and said sealring shoulder.

8. The universal medical connector assembly of claim 4, wherein;

each of said at least two fingers is resiliently outwardly expandable such that when said at least two fingers are outwardly expanded said piston can be moved past said at least one piston retaining stop toward said open end.

9. The universal medical connector assembly of claim 1, wherein said elongated housing is of one-piece construction.

* * * * *